United States Patent [19]

Bilstad et al.

[11] Patent Number: 4,493,693

[45] Date of Patent: Jan. 15, 1985

[54] TRANS-MEMBRANE PRESSURE MONITORING SYSTEM

[75] Inventors: Arnold C. Bilstad, Deerfield; John T. Foley, Wheeling; Walker P. Woodworth, Vernon Hills, all of Ill.

[73] Assignee: Baxter Travenol Laboratories, Inc., Deerfield, Ill.

[21] Appl. No.: 403,362

[22] Filed: Jul. 30, 1982

[51] Int. Cl.³ .......................... A61A 1/03; B01D 19/00
[52] U.S. Cl. ........................................ 604/6; 128/630
[58] Field of Search ........................... 604/4–6; 210/90, 97, 927; 128/630

[56] References Cited

U.S. PATENT DOCUMENTS

| | | |
|---|---|---|
| 3,366,240 | 1/1968 | Gruber . |
| 3,412,706 | 11/1968 | Topol et al. . |
| 3,429,291 | 2/1969 | Hoffman . |
| 3,548,662 | 12/1970 | Brandau et al. . |
| 3,572,319 | 3/1971 | Bittner et al. . |
| 3,795,318 | 3/1974 | Crane et al. . |
| 3,900,290 | 8/1975 | Hornstra . |
| 3,946,731 | 3/1976 | Lichtenstein . |
| 3,990,066 | 11/1976 | Malmgren . |
| 4,006,430 | 2/1977 | Meyer-Ebrecht . |
| 4,021,341 | 5/1977 | Consentino et al. . |
| 4,080,966 | 3/1978 | McNally et al. . |
| 4,098,274 | 7/1978 | Ebling et al. . |
| 4,107,037 | 8/1978 | Cavanaugh et al. ................. 210/902 |
| 4,113,614 | 9/1978 | Rollo et al. . |
| 4,148,314 | 4/1979 | Yin . |
| 4,153,554 | 5/1979 | von der Heide et al. . |
| 4,191,182 | 3/1980 | Popovich et al. . |
| 4,192,005 | 3/1980 | Kurtz . |
| 4,209,391 | 6/1980 | Lipps et al. . |
| 4,231,366 | 11/1980 | Schael . |
| 4,303,068 | 12/1981 | Zelman .................................. 604/5 |

FOREIGN PATENT DOCUMENTS 8102979 10/1981 World Intel. Prop. Org. ........ 604/6

Primary Examiner—Edward M. Coven
Attorney, Agent, or Firm—Paul C. Flattery; Eugene M. Cummings; Daniel D. Ryan

[57] ABSTRACT

A monitoring system for monitoring trans-membrane pressure in plasmapheresis apparatus utilizing a microporous membrane type filter includes first and second pressure-to-frequency transducer circuits for developing signals frequency-indicative of the inlet and outlet pressures of the filter. The signals are digitally compared in a pulse subtraction circuit to produce an output signal frequency-indicative of trans-membrane pressure. The output signal is applied to a periodically reset display counter to develop a digital readout of trans-membrane pressure. Porous filter elements in the flow system and in the inlet port of each transducer isolate bacteria within the flow system, prevent contamination of the transducers, and provide a time constant for each transducer which prevents transient flow variations in the system from causing erroneous trans-membrane pressure readings.

17 Claims, 13 Drawing Figures

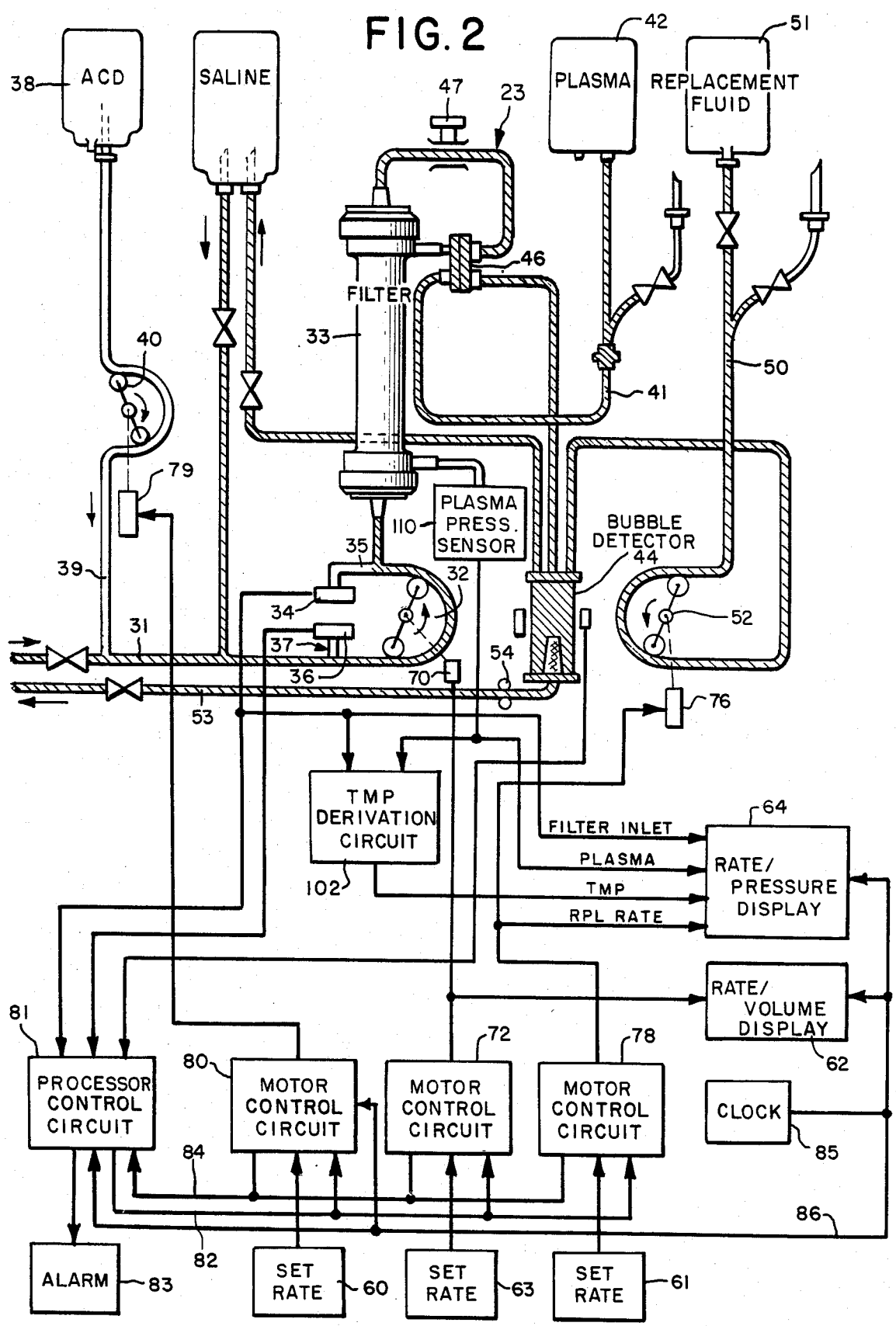

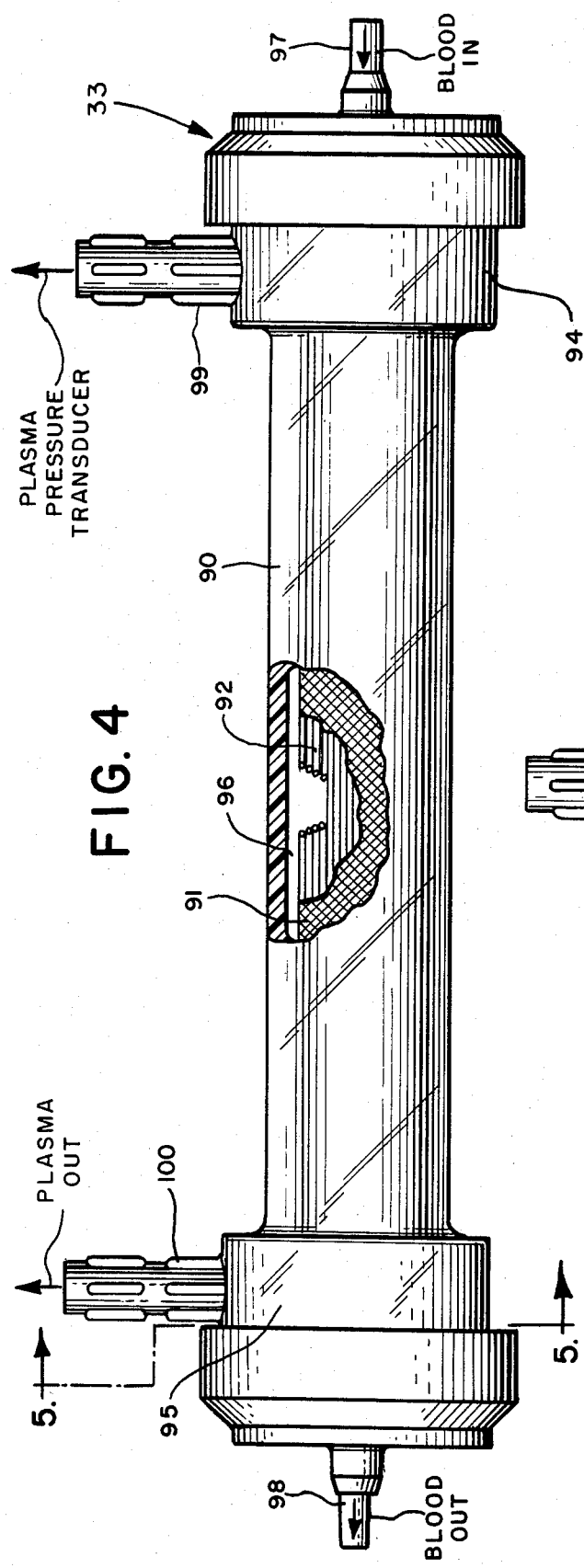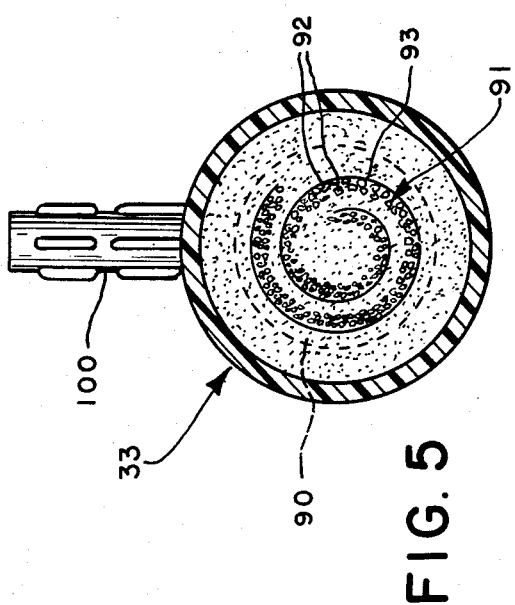

TRANS-MEMBRANE PRESSURE MONITORING SYSTEM

BACKGROUND OF THE INVENTION

The present invention relates generally to membrane-type separation and fractionation apparatus for separating and collecting a desired component from a whole fluid, and more specifically to a pressure monitoring system for monitoring trans-membrane pressure in such apparatus.

Microporous membrane filter devices have come into wide use in selective separation and purification procedures, such as hemodialysis and plasmapheresis, for separating a desired fluid component from a continuously flowing whole fluid. Typically, such filter devices are incorporated in a disposable flow system, which is installed in a processing apparatus during the procedure, and then disposed of after a single use.

In a preferred form the filter devices take the form of a bundle of parallel microporous hollow fibers arranged side-by-side in the form of a bundle within a hollow cylindrical housing. As the whole fluid is caused to flow through the fibers the desired fluid component passes through the walls of the fiber membrane to the surrounding container, which forms a collection chamber from which the separated component is transported to a collection device. A preferred construction and method of manufacture of such a hollow fiber filter is shown in the copending application of Robert Lee and William J. Schnell, entitled, "Microporous Hollow Fiber Membrane Assembly and Its Method of Manufacture", Ser. No. 278,913, filed June 29, 1981. A preferred apparatus for use with a hollow fiber filter is shown in the copending applications of Arnold C. Bilstad et al; entitled, "Blood Fractionation Apparatus", Ser. No. 330,898; entitled, "Blood Fractionation Apparatus having Collected Volume Display", Ser. No. 330,899; entitled, "Blood Fractionation Apparatus have Collection Rate Display", Ser. No. 330,901; and entitled, "Blood Fractionation Apparatus having Replacement Fluid Rate Control System", Ser. No. 330,900, all filed Dec. 15, 1981, and assigned to the present assignee.

In microporous membrane devices the walls of the membrane have pores which are permeable to air and other gases, thereby permitting air and gases to readily pass through. However, notwithstanding their air-permeable nature, the walls retain a semi-permeable or permselective characteristic and serve to restrict the flow of a liquid passing through them, as in blood oxygenators, or to restrict the flow of a component of the liquid passing through, such as blood cells in membrane plasmapheresis devices. Materials from which a microporous hollow fiber filter element can be made include thermal plastic polymers, such as polypropylene. These polymers can be formed into hollow fibers by known processes such as solution or melt spinning.

The efficient operation of membrane-type filter devices, particularly hollow-fiber type devices in continuous flow plasmapheresis apparatus, requires that the pressure differential between the supply and collection sides of the hollow fiber membrane, termed trans-membrane pressure (TMP), be monitored and maintained within predetermined operational limits.

A preferred equalizer valve apparatus and method for adjusting TMP pressure in a hollow fiber filler system is shown in the copending applications of Clinton Kopp et al; entitled, "Membrane Plasmapheresis Apparatus and Procedure", Ser. No. 277,428; entitled, "Fluid Flow Control Device", Ser. No. 277,449; and entitled, "Fluid Flow Control Device", Ser. No. 277,414; all filed June 25, 1981 and assigned to the present assignee.

Allowing the TMP pressure to become too high in any portion of the filter may result in undesired blood components, such as RED blood cells, restricting or clogging the membrane, or may cause red blood cells to rupture or lyse as they flow through the filter assembly. Allowing the TMP pressure to be too low may result in inefficient operation of the filter, since the desired component does not readily flow through the filter membrane. Accordingly, it is desirable that continuous flow filter-type separation and fractionation apparatus include a system for monitoring trans-membrane pressure.

One requirement of any trans-membrane pressure monitoring system is that it provide a continuous output reading, preferably in digital form, which can be quickly and easily interpreted by an operator of the apparatus. Furthermore, the system must not interfere with the operation of the apparatus or the associated disposable flow system, and must not compromise the sterility of the flow system or allow bacterial contamination of the apparatus or the surrounding environment by the fluid being processed. The present invention is directed to a monitoring system which meets these requirements by providing in a plasmapheresis apparatus or the like a continuous digital readout of TMP without compromise to the operation or bacterial isolation of the associated flow system.

The TMP monitoring system of the present invention may be constructed to read TMP between the whole blood inlet and the plasma outlet of a hollow fiber membrane filter, as shown in the illustrated embodiment, thereby displaying the maximum TMP present in the filter, or may be constructed to read whole blood pressure at one or more alternate locations, or, at both the whole blood inlet and outlet, to display the average TMP in the filter.

In a preferred form of the TMP monitoring system of the present invention disposable pressure transducer isolators are provided to prevent bacterial contamination. These isolators, which comprise a microporous synthetic polymer barrier having sufficient porosity to allow passage of gas, but insufficient porosity to prevent passage of bacteria, are constructed in accordance with the teachings of the copending application of Arnold C. Bilstad et al, entitled "Pressure Transducer Isolator and Method", Ser. No. 353,546, filed Mar. 1, 1982. In addition to providing isolation between the disposable fluid flow system and the pressure transducers, these pressure isolators provide integration or modulation of pressure variations in the system to prevent such variations from affecting the TMP readings developed by the monitoring system. Moreover, these isolators are relatively low in cost and sterilizable by conventional sterilization techniques, making their inclusion in disposable flow systems feasible.

Accordingly, one of the principal objects of the present invention is to provide a new and improved trans-membrane pressure monitoring system for use in conjunction with a filter device in a fluid separator or fractionation apparatus, such as utilized for hemodialysis and plasmapheresis.

Another principal object of the invention is to provide a trans-membrane pressure monitoring system for use in plasmapheresis apparatus and the like which does not interfere with the operation of the apparatus and which provides a continuous easily readable display of trans-membrane pressure.

Another principal object of the invention is to provide a trans-membrane pressure monitoring system for use in plasmapheresis apparatus or the like which is not subject to contamination by bacteria or microorganisms in fluid being processed.

SUMMARY OF THE INVENTION

To achieve the use and other objects, the trans-membrane pressure monitoring system of the invention provides in a fluid processing apparatus and associated fluid flow system having a microporous membrane filter element a first pressure responsive transducer coupled to the flow system at the input of the filter element for providing a first signal indicative of inlet pressure to the element. A second pressure responsive transducer is coupled to the collection chamber of the filter device to provide a second pressure signal indicative of output pressure from the filter. A trans-membrane pressure derivation circuit develops an output signal indicative of trans-membrane pressure from the two pressure signals. The output signal is applied to a display circuit which develops a readout of trans-membrane pressure.

In a preferred embodiment of the invention, the signals produced by the transducers are frequency-indicative of applied pressure, and each transducer means include a time constant which prevents pressure variations associated with operation of pumps in the apparatus from affecting frequency of the output signals. The frequency indicative transducer output signals are compared by digital circuitry in the trans-membrane pressure derivation circuit to develop a frequency indicative trans-membrane pressure output signal which is digitally displayed by the display circuit.

In a further preferred embodiment, the transducer time constants are provided by one or more porous isolator elements in line with respective ones of the transducers. At least one element associated with each transducer is advantageously located in the disposable flow system to eliminate the need for a separate liquid blocking filter element, and at least one element associated with each transducer is advantageously located at the pressure inlet to the transducer to prevent contamination of the transducer and the processing apparatus by fluid in the disposable flow system.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 2 is a functional block diagram partially in schematic form showing the principal components of the plasmapheresis apparatus of FIG. 1.

FIG. 4 is a front elevational view, partially in cross-section of a hollow-fiber microporous membrane filter element utilized in the plasmapheresis apparatus of FIG. 1.

FIG. 5 is a cross-sectional view of the hollow-fiber filter element taken along line 5—5 of FIG. 4.

DESCRIPTION OF THE PREFERRED EMBODIMENT

Figure 1:
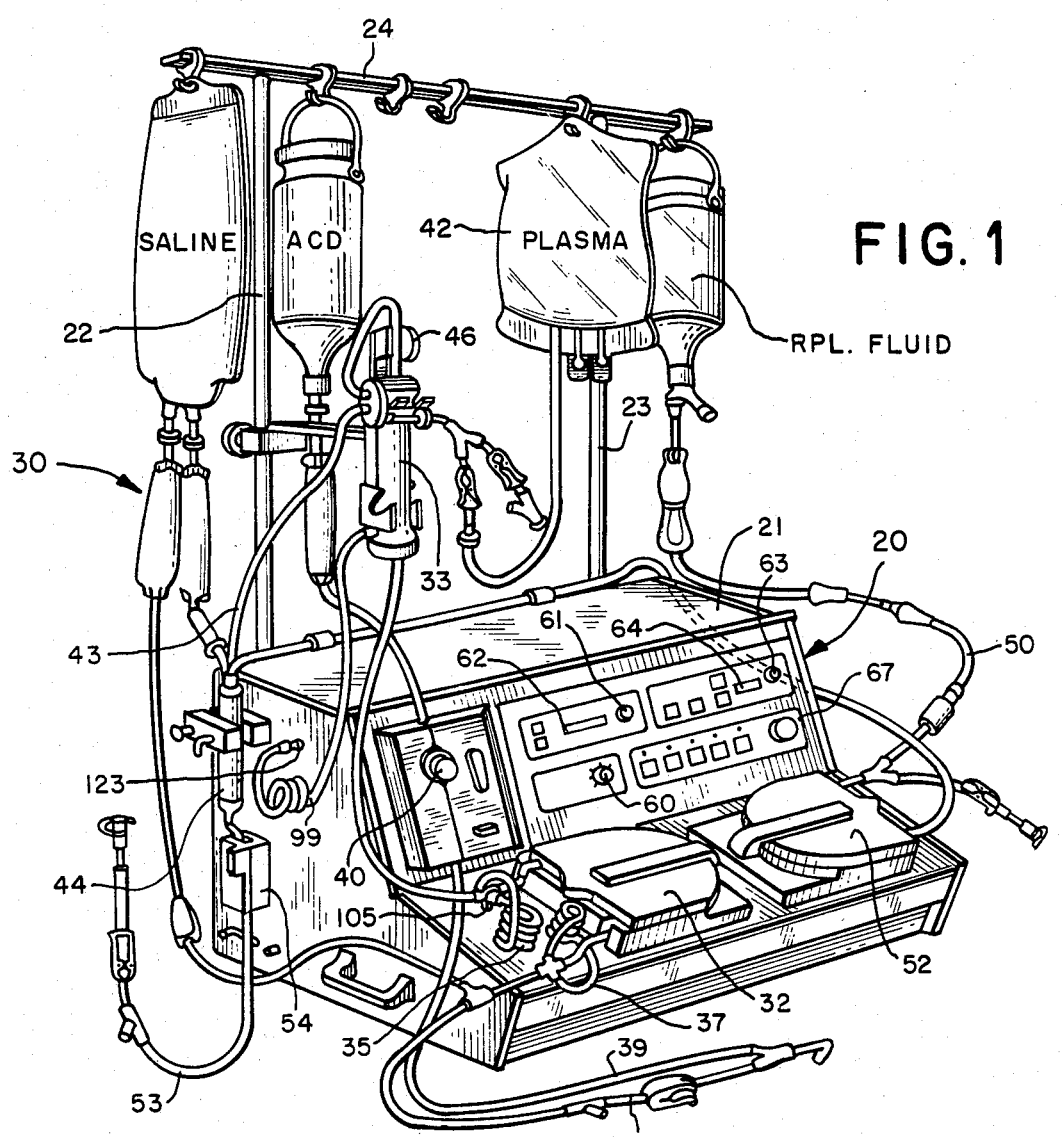
FIG. 1 is a perspective view of plasmapheresis apparatus incorporating a trans-membrane monitoring system constructed in accordance with the invention.

Referring to the figures, and particularly to FIG. 1, a plasmapheresis apparatus 20 incorporating a TMP monitoring system in accordance with the present invention is seen incorporated within a table-mounted housing 21. The housing preferably includes a pair of vertical support poles 22 and 23 from which a horizontal bar 24 is mounted to allow a plurality of collection and dispensing containers of conventional construction to be hung by means of appropriate hangers.

The processing apparatus 20 operates in conjunction with a disposable fluid circuit, generally identified by the reference numeral 30 in FIG. 1 and shown schematically in FIG. 2. The fluid circuit 30 includes a plurality of flexible plastic tubing segments which form fluid conduits between various components of the fluid circuit. As shown in FIG. 2, whole blood derived from a donor is conveyed through a first tubing segment 31 and a peristaltic-type whole blood (WB) pump 32 to a hollow fiber-type filter 33 mounted on support rod 22. The operation of the WB pump is monitored by a positive pressure (+P) monitor circuit 34 connected to tubing segment 31 downline of the WB pump by a tubing segment 35. Negative pressure, such as might occur upon the collapse of a vein, is monitored for by means of a negative pressure (−P) monitor circuit 36 connected to tubing segment 31 upline of the WB pump 32 by a tubing segment 37.

To prevent blood from clotting while in process in the apparatus anticoagulant solution from a supply container 38 is introduced at the point of blood withdrawal through a tubing segment 39. A peristaltic-type pump 40 is provided along tubing segment 39 to provide a controlled rate of addition of the anticoagulant fluid to the whole blood.

Plasma separated from the whole blood within the hollow fiber filter 33 is conveyed by a tubing segment 41 to a plasma collection container 42. The pressure provided by WB pump 32 is sufficient to cause flow through the filter to the collection container. The plasma-deficient processed blood from filter 33 is conveyed through a tubing segment 43 to an ultrasonic bubble detector 44, which may be similar in structure and operation to that described in copending application of Arnold C. Bilstad and Michael Wicnieski, entitled, "Liquid Absence Detector", Ser. No. 127,552, filed Mar. 6, 1980.

To equalize pressure between the plasma-deficient and collected plasma outlets of filter 33 an equalizer valve 46 is provided at the filter plasma outlet port. Basically, this equalizer valve functions to restrict the plasma outlet port until the pressure of the plasma in the filter reaches that of plasma-deficient blood flowing from the filter, at which time the valve modulates plasma flow through line 41 to the collection container 42. An adjustable occlusion device 47 provided in line 42 between filter 33 and the equalizer valve 46 allows the pressure differential between the collected plasma and the plasma-deficient blood to be adjusted by the user. As will be seen presently, the TMP monitoring system of the invention provides a readout of this transmembrane pressure to assist the user in making the required adjustment from maximum operating efficiency of filter 33.

Replacement fluid is added to the plasma-deficient blood at bubble detector 44 through a tubing segment 50 which is connected at one end to a replacement fluid container 51 and at its other end to the housing of bubble detector 44. A peristaltic-type replacement pump 52 is positioned along tubing segment 50 to establish a controlled flow rate for the replacement fluid. The combined plasma-deficient whole blood and replacement fluid are pumped from bubble detector 44 back to the donor through a tubing segment 52. A safety clamp 54 positioned along tubing segment 53 downline of bubble detector 44 actuates in the event of a malfunction in the apparatus to prevent uncontrolled infusion of fluid into the patient.

Figure 3:
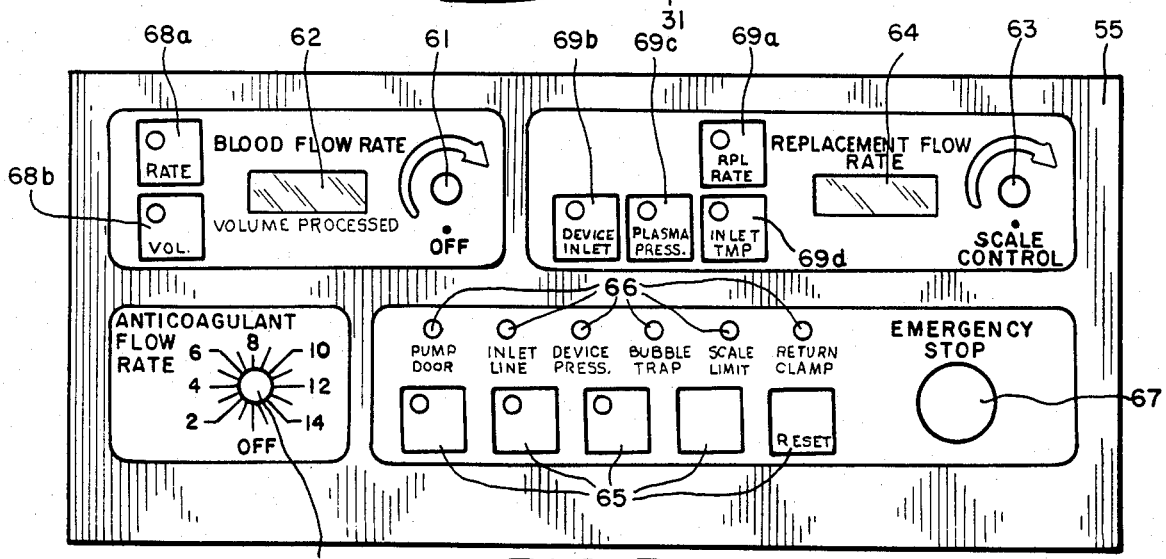
FIG. 3 is an enlarged front elevational view of the control panel of the plasmapheresis apparatus of FIG. 1.

As shown in FIG. 1, the plasmapheresis apparatus 20 includes a sloped control panel 55 which includes operator-actuated controls for operating the plasmapheresis apparatus. Referring to FIG. 3, control panel 55 is seen to include a selector switch 60 by which the operating speed of the anticoagulant pump 40 is set, a potentiometer control 61 and digital readout 62 by which the operating speed of the WB pump 32 is controlled, and a potentiometer 63 and digital readout 64 by which the operating speed of the replacement pump 52 is controlled. A plurality of push button switches 65 are provided to establish the operating mode of the apparatus, and a plurality of status-indicating lights 66 provide indications of malfunctions in the system. An emergency stop switch 67 provides for an immediate operator-initiated shut down in the event of a malfunction.

Additional display functions are provided for display 62 by momentary actuation of push button switches 68a and 68b. Switch 68a causes indicator 62 to display WB flow rate. Actuation of switch 68b causes display 62 to display the total volume of whole blood processed by the apparatus since beginning an operating cycle. Additional functions for display 64 are provided by push button switches 69a–69d. Actuation of switch 69a causes a flow rate of the replacement fluid to be displayed. Actuation of switch 69b causes the inlet pressure of pressure device 33 to be displayed. Switch 69c causes the collected plasma pressure of device 33 to be displayed. Actuation of switch 69d causes the transmembrane pressure (TMP) of the filter device to be displayed as derived by the TMP monitoring circuit of the invention.

Referring to FIG. 2, the whole blood pump 32 is driven by a motor 70. Power for operating motor 70 is provided by a motor control circuit 72 which responds rate setting means in the form of potentiometer control 63 and a tachometer feedback signal from a tachometer (not shown) associated with motor 70 to maintain a desired motor operating speed. The actual pump flow rate is displayed by readout 62 as part of a display circuit which receives the tach output signal.

Similarly, the replacement pump 52 is driven by a motor 76. Power for motor 76 is provided by a motor control circuit 78 which responds to a tach feedback signal from a tachometer (not shown) associated with the motor and the rate selected by the panel-mounted potentiometer 61 to maintain a desired constant motor speed. The actual pump flow rate is displayed by readout 62 as part of a display circuit.

The anticoagulant pump 40 is driven by a stepper motor 79. Drive signals for motor 79 are developed by a motor control circuit 80 which responds to rate selection switch 60 to maintain a desired anticoagulant flow rate. A tachometer (not shown) associated with motor 79 provides tach pulses for use by control circuit 80.

The operation of the various pump motors is controlled by a processor control circuit 81 which includes the five mode select push button switches 65 on front panel 55. System malfunctions, such as negative pressure at pressure monitor 36, or excessive positive pressure at pressure monitor 34, or the occurrence of a bubble or other fluid absence as signaled at the output of bubble detector 44, result in the application of an alarm signal to processor control circuit 81. This circuit responds by producing a control signal on a first motor control line 82 to the motor control circuits 72, 78 and 90 to interrupt operation of the motors. In addition, an alarm 83 associated with the processor control circuit may be sounded and an appropriate one of indicator lamps 66 may be lit to alert the operator. In addition, each of motor control circuits 72, 78 and 80 includes internal stall protection whereby an alarm signal is developed and applied to processor control circuit 81 on a control line 84 to terminate operation of the plasmapheresis apparatus 20 in the event of a pump malfunction. A system clock circuit 85 may be provided to supply clock pulses necessary for the operation of display circuits 61 and 62, processor control circuit 81, and motor control circuit 80 along a distribution line 86.

Referring to FIGS. 4 and 5, the hollow-fiber membrane-type filter device 33 employed in plasmapheresis apparatus 20 includes a generally cylindrical housing 90 within which a bundle 91 of microporous hollow fibers 92 is mounted on a carrier sheet 93. In accordance with the teaching of the previously identified U.S. patent Ser. No. 278,913, the carrier sheet is formed into a spiral such that the individual fibers 92 extend lengthwise along the axis of the cylindrical housing 90.

The housing includes end caps 94 and 95 which close the ends to form a plasma collection chamber 96 within the housing. The fiber bundle 91 is carried within the interior chamber 96 in a loose, inwardly rolled configuration, as shown in FIG. 5.

When assembled, filter device 33 includes a whole blood inlet port 97 formed on end cap 94, and a whole blood outlet port 98 formed on the other end cap 95. Blood introduced through the port 97 enters the adjoining open ends of the hollow fiber membrane elements 92 and proceeds to flow lengthwise through the fibers. By maintaining a desired level of trans-membrane pressure, plasma in the whole blood is caused to flow through the micropores of the hollow fibers 92 and out into the collection chamber 96 circumferentially surrounding the bundle 91.

Housing 90 includes two side plasma outlet ports 99 and 100 which communicate with the collection chamber 96 to enable plasma to be withdrawn from the filter. In plasmapheresis apparatus 20, plasma outlet port 100 is utilized to withdraw plasma from the filter, and plasma outlet port 99 is advantageously used to sense plasma outlet pressure in conjunction with the TMP onitoring system of the invention.

The remaining ends of the hollow fiber filter elements 92 are jointed together at end cap 95 so as to communicate with blood outlet port 98. Plasma-poor blood (containing red cells, leukocytes and platelets), having passed through the hollow fiber membrane elements, exits through outlet port 98, typically for return to the patient-donor.

Because of their comparitively high efficiency in separating plasma from continuously flowing whole blood, hollow-fiber filters have proven particularly advantageous for use in continuous flow plasmapheresis system such as that illustrated herein. However, to realize the full efficiency potential of this type of filter it is important that the transmembrane pressure (TMP) of the hollow fiber filter elements be carefully controlled and maintained within defined operating limits. To this end, plasmapheresis apparatus 20 includes, in accordance with the invention, a system for continuously monitoring and digitally displaying TMP.

Figure 6:
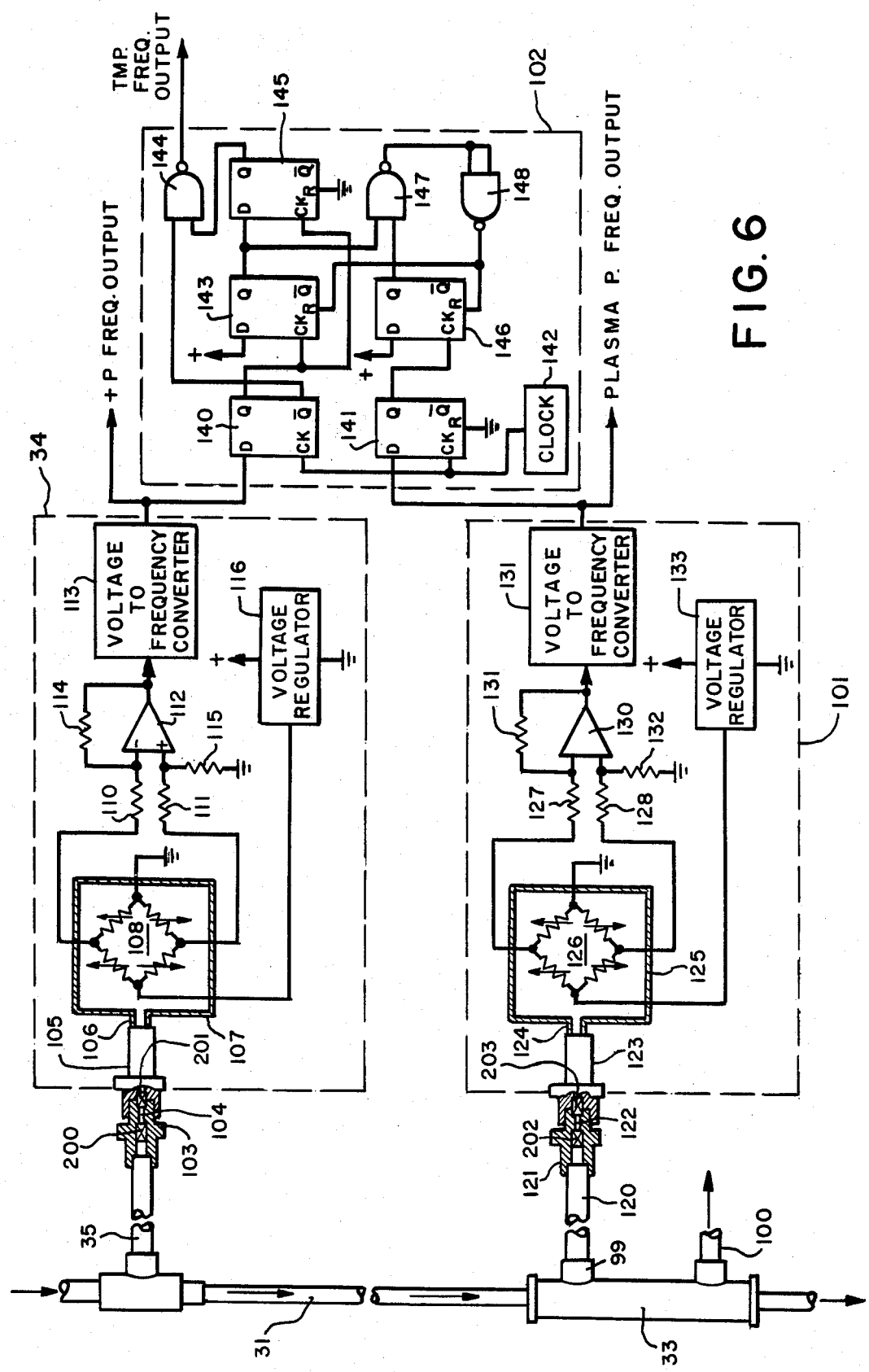
FIG. 6 is a simplified schematic diagram partially in functional block form of the trans-membrane pressure monitoring system of the invention as incorporated in the plasmapheresis apparatus of FIG. 1.

Referring to FIG. 6, the TMP monitoring system of the invention is seen to include the previously described positive pressure monitor circuit 34 located at the output of whole blood pump 32, a plasma pressure monitor circuit 101, and a digital pulse subtraction circuit 102. As previously described, whole blood pressure down-line of WB pump 32 is applied to the +P monitor thru segment 35, which is connected to segment 31 by a conventional T-fitting 102 or other appropriate means. The free end of segment 35 is preferably provided with a connector 103 formed of molded plastic or the like and including a threaded plug portion 104 or other appropriate means for detachable engagement with the +P monitor 34. The monitor circuit 34 preferably includes a socket 105 at a convenient location on the front panel of housing 21 for receiving plug 103 in locking engagement. Socket 105 may be connected by a tubing segment 106 to an electrical pressure transducer 107 of conventional construction, which serves to translate pressure changes conveyed through tubing segment 35, plug 103, socket 105 and tubing segment 106 to resistance changes in an internal bridge circuit 108. Transducer 107, in accordance with conventional practice, forms a resistive bridge network 108 wherein the output resistance varies as a function of applied pressure. The output terminals of this bridge network are connected through respective resistors 110 and 111 to the inverting and non-inverting inputs of a differential amplifier 112.

The output of this amplifier, which depends on the applied differential voltage, and hence on the pressure applied to transducer 107, is connected to a voltage-to-frequency converter 113. The output and inverting input of amplifier 112 are connected through resistor 114 to provide degenerative feedback. The non-inverting input of amplifier 112 is connected to ground by a resistor 115 in accordance with conventional practice. A regulated reference voltage is applied to one input terminal of resistance bridge 108 by a voltage regulator 116. The other input terminal of bridge 108 is connected to ground.

Voltage-to-frequency converter 113 responds to the applied voltage developed by differential amplifier 112 to produce an output having a frequency related to the pressure present at transducer 107. This pressure-indicative signal is applied to display circuit 61, wherein it is utilized to produce a display of filter inlet pressure upon actuation of push button switches 69b (FIG. 3), and to derivation circuit 102.

The operation of the plasma pressure monitor circuit 101 is similar to that of +P monitor circuit 34. Plasma pressure is sensed at outlet port 99 of filter device 33 by means of a tubing segment 120 which includes at its free end a plug 121 similar to plug 103. Plug 121 includes a projecting portion 122 which may be threaded for locking engagement with a socket 123 located on the side panel of housing 21. Within plasma monitor circuit 101 a pressure conveyed to socket 123 is conveyed through a tubing segment 124 to an electrical pressure transducer 125. This transducer, which may be identical to transducer 107, includes a bridge circuit 126 having output terminals connected through a pair of resistors 127 and 128 to a differential amplifier 130. The output of amplifier 130, which depends on the differential between the signals applied to its input terminals, and hence on the pressure applied to transducer 126, is applied to a voltage-to-frequency converter 131. A resistor 132 connected between the output of amplifier 130 and the inverting input of the device provides degenerative feedback. A resistor 132 is connected between the non-inverting input and ground in accordance with conventional practice. A regulated reference voltage is applied to the input terminals of transducer bridge 126 by a voltage regulator 133 of conventional design.

Voltage-to-frequency converter 131 responds to the applied voltage from differential amplifier 130 to produce an output having a frequency related to the pressure present at transducer 125. This pressure-related signal is applied to display circuit 61 (FIG. 2), wherein it is utilized to provide an output display of plasma outlet pressure upon actuation of push button switch 69c (FIG. 3), and to the digital subtraction circuit 102 of the TMP monitoring system.

The derivation circuit 102 functions to develop an output signal frequency-indicative of the difference in frequency between the +P output signal developed by monitor circuit 34, and the plasma pressure output signal developed by monitor circuit 101. To this end, circuit 102 includes a first D-type flip-flop 140 to which the +P signal is applied, and a second D-type flip-flop 141 to which the plasma pressure frequency signal is applied. A source of clock pulses 142, which may be located within derivation circuit 102 as shown, or which may be provided from an external pulse source, such as the apparatus clock 85, provide clock pulses to flip-flops 140 and 141 such that these devices change output state only upon receipt of a pulse from their associated pressure-indicative source and the subsequent occurrence of a clock pulse. Upon this happening, flip-flop 140 changes state, providing a clock pulse to a third flip-flop 143 and an enabling signal from its $\overline{Q}$ output to one input of a NAND gate 144. The D input of flip-flop 143 is connected to a positive voltage source, causing that device to immediately switch state in response to the applied pulse from flip-flop 140. The resulting change in state at the Q output of this flip-flop is applied to a fourth flip-flop 145, which does not change state pending receipt of a subsequent clock pulse. Since flip-flop 145 does not change state, NAND gate 144 is inhibited and no TMP output is produced. However, with subsequent +P-indicative pulses applied to flip-flop 140, flip-flop 143 is in a toggled condition, so that flip-flop 145 is toggled to provide an enabling signal at NAND gate 144 which allows the second and all subsequent applied +P monitoring pulses to appear as TMP-indicative output pulses.

Upon application of a plasma pressure-indicative pulse to flip-flop 141, upon occurrence of the next-occurring clock pulse a fifth flip-flop 146 is caused to toggle by reason of its D input being connected to a positive voltage source. A Q output of this flip-flop is connected to one input of a second NAND gate 147, enabling that device. The other input of NAND gate 147 is connected to the Q output of flip-flop 143, such that when the NAND gate is enabled an output pulse is produced and applied through a buffer 148 to the reset inputs of flip-flops 143 and 146. This causes the flip-flops to revert to a non-toggled state, pending the application of a subsequent clock pulse from flip-flops 140 and 141, respectively.

As a consequence of flip-flop 143 being reset, flip-flop 145 reverts to a non-toggled condition upon occurrence of the subsequent clock signal applied by flip-flop 140, which causes NAND gate 144 to be inhibited and no TMP output pulse to be produced upon occurrence of the subsequent +P pressure pulse. Upon occurrence of the next subsequent pulse however, flip-flop 143 again reverts to a toggle state, causing flip-flop 145 to toggle and NAND gate 144 to be enabled.

Thus, the operation of the digital subtraction circuit 102 is such that each occurrence of a plasma pressure pulse results in one +P pressure pulse not being conveyed to the TMP output. Since the occurrence of pulses is directly related to the frequency of the two pressure signals, which in turn is related to the inlet and plasma pressures associated with filter device 33, circuit 102 functions to produce an output signal having a frequency related to the difference between the inlet and outlet pressures at the filter device. This TMP frequency-indicative output signal is applied to display circuit 61 (FIG. 2), wherein it is displayed upon actuation of push button switch 69d (FIG. 3).

Figure 7:
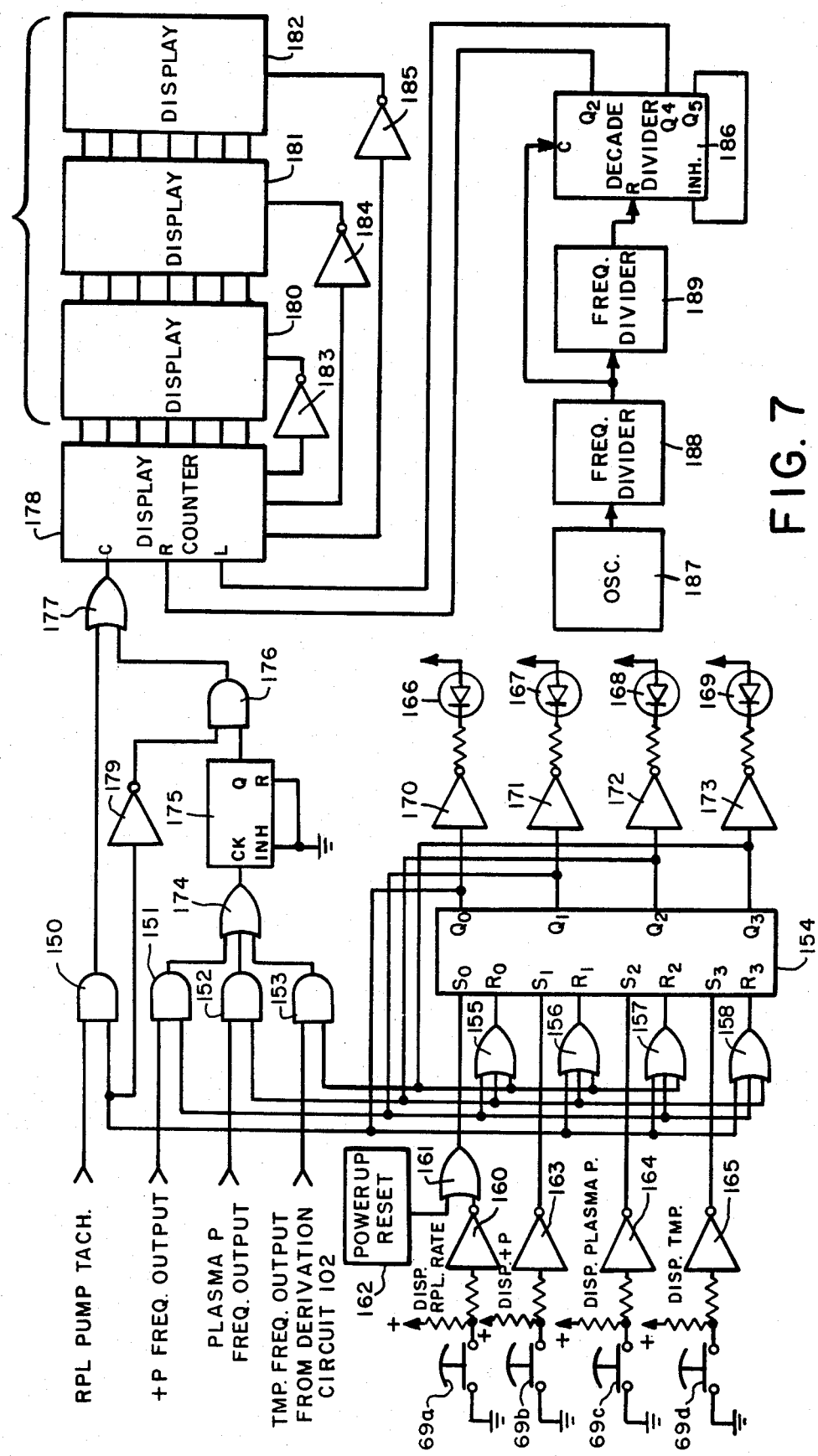
FIG. 7 is a simplified schematic diagram partially in functional block form of the display circuitry of the plasmapheresis apparatus utilized in conjunction with the trans-membrane pressure monitoring system of FIG. 6.

Referring to FIG. 7, the display circuit 64 may comprise a plurality of AND gates 150-153 for receiving the replacement pump tach, +P frequency output, plasma pressure frequency output and TMP frequency output signals. A selected one of these AND gates 150-153 is enabled by a four-section latch device 154 having outputs $Q_0-Q_3$ connected to respective ones of control lines 155-158 associated with the remaining input terminals of the four AND gates.

Selection of the particular input is accomplished by momentary actuation of the appropriate one of switches 69a-69d. Switch 69a is connected through an inverter 160 and OR gate 161 to the set input of the first section of the four-section flip-flop 154 to condition that section to a set condition and thereby enable AND gate 150 through control line 155 upon actuation of the switch. A second input of OR gate 161 is connected to a power up reset circuit 162 to provide a similar result upon initial power up of the plasmapheresis apparatus.

The +P inlet pressure is displayed by actuation of switch 69b, which conditions the second section of the RS flip-flop 154 to a set state through an inverter 163. This provides an enabling signal on control line 156 which enables AND gate 151. Similarly, the plasma pressure display is obtained by momentary actuation of switch 69c, which enables the third section of RS flip-flop 154 through an inverter 164. The TMP display is obtained by momentary actuation of switch 69d, which conditions the fourth section of flip-flop 154 through an inverter 165.

An indication of the active input is provided by four light emitting diodes 166-169 connected by respective ones of four inverters 170-173 to the four outputs of flip-flop 154. Indicator lamps 166-169 may be advantageously combined with push button switch 69a-69d, as shown in FIG. 3.

A selected one of the inlet pressure, plasma pressure and TMP frequency-indicative signals is applied through an OR gate 174 to the clock input of a counter 175. The output of counter 175, delayed by the action of the counter is applied through an AND gate 176 and an OR gate 177 to the clock input of a display counter 178. In the event that the replacement fluid pump rate is selected and control line 155 is enabled, AND gate 176 is inhibited by the output of an inverter 179 connected to control line 155. AND gate 150 being then enabled, replacement pump tach signals are applied directly through OR gate 177 to display counter 178.

Counter 175 is said to divide by a factor of 10, producing one output pulse for each 10 clock pulses applied by OR gate 174.

Display counter 178, which may be conventional in structure and operation, responds to the applied pulses to accumulate a count indicative of the selected input to be displayed. At the end of a measurement period, in the present embodiment one second, a latch pulse is applied to the counter to the cause in a conventional manner to assume the accumulated count and provide an appropriate driving signal for a trio of associated seven segment display panels 180-182, which comprise readout 64 on control panel 55. Appropriate strobe pulses for enabling displays in a conventional manner are provided by counter 178 through respective ones of inverter amplifier 183-185.

Following the latch pulse, after the display counter has assumed at its output the previously accumulated count, the accumulated count is reset by a reset clock pulse applied to the reset input of the counter. This reset pulse, and a corresponding latch pulse, are developed at a one second repetition rate by a Johnson counter 186, which may comprise part of the system clock circuit 85. This counter is clocked by a one hertz signal obtained from a clock circuit which includes an oscillator 187 and a pair of frequency dividers 188 and 189 of conventional design. Since alternate outputs of the Johnson counter are utilized, the latch pulse leads and is distinct from the reset pulse, so that counter 178 completes its latch function before it begins its reset function, thus assuring that the counter will display the preceding count during the subsequent one second counting interval.

The same display counter 178 displays fluid pressure upon momentary actuation of one of push button switches 69b-69d. This causes AND gate 150 to be inhibited and AND gate 176 to be enabled through inverter amplifier 179. As a result, the variable-frequency pressure-indicative pulses appearing at the selected ones of the pressure signal inputs, which each represent ten hertz per millimeter of mercury, are supplied to display counter 178 through OR gate 174, divide-by-ten counter 175, and OR gate 177. Since counter 178 continues to be reset once each second, the counter in effect measures the frequency in hertz per second, which translates directly to millimeters of mercury. An indication is given of the display selected for readout 64 by LED indicators 166–169.

Reference is made to the previously identified copending application of Arnold C. Bilstad et al, Ser. No. 330,898 for a detailed explanation of the display circuit and its associated control circuitry.

Figure 8:
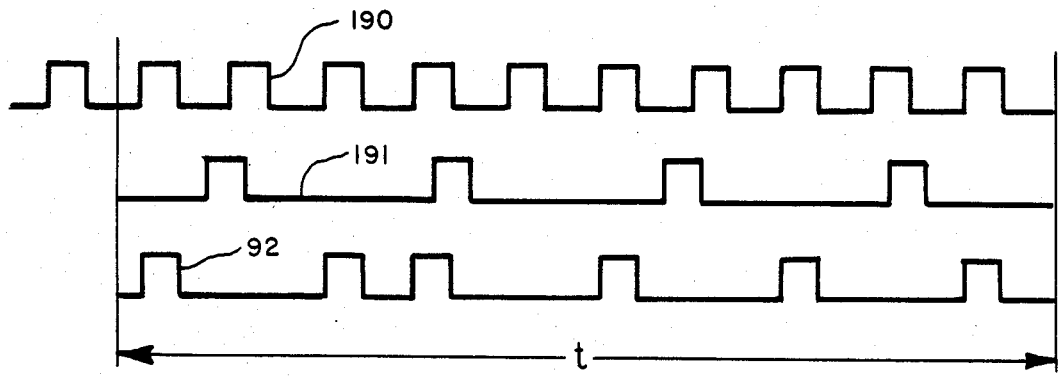
FIG. 8 is a depiction of certain waveforms useful in understanding the operation of the trans-membrane pressure monitoring system of the invention.

Thus, in operation the TMP monitoring circuit of the invention provides for generation of a first signal indicative of filter inlet pressure, and a second signal indicative of plasma outlet pressure. These signals are subtracted in a derivation circuit 102 to obtain a variable-frequency TMP-indicative output signal which is selectively displayed by display counter 178 upon actuation of the corresponding display select push button switch 69d. In the preferred embodiment, the inlet and plasma pressure monitoring circuits 34 and 101 produce, in accordance with an aspect of the invention, variable-frequency pressure-indicative signals which are digitally subtracted by derivation circuit 102 to obtain a variable-frequency TMP-indicative output signal suitable for application to display counter 178. The operation of this preferred arrangement is illustrated in FIG. 8, wherein an inlet pressure waveform 190 is produced by voltage-to-frequency converter 113, and an input waveform 191 illustrates a waveform of lesser frequency produced by voltage-to-frequency converter 131. The resulting TMP-indicative output signal, taken over a measurement period t, is seen to equal the frequency difference between the two applied signals.

To prevent transitory variations in fluid pressure such as might occur from operation of the peristaltic pumps of the apparatus from effecting the TMP display, it is desirable that the pressure monitoring circuits 34 and 101 include appropriate means for introducing an integration factor of time constant and their response to applied pressure changes. To this end, in accordance with another aspect of the invention, the pressure communication channels between transducers 107 and 125 and the disposable flow system may include pressure isolators in the form of sterile, microporous polymer barriers inserted in the channels, which have sufficient porosity to allow passage of gas but not bacteria, and which provide a predetermined integration factor sufficient to reduce the effect of short term pressure variations on the transducers.

In the preferred embodiment, each pressure communication channel includes two isolators, one associated with the integral to the disposable flow system, and the other associated with and integral to the pressure monitoring system of the apparatus. Referring to FIG. 6, in the input pressure channel a first isolator device 200 is provided in plug 103 and a second isolator device 201 is provided in receptacle 105. In the plasma pressure channel, a first isolator device 202 is provided in plug 121 and a second isolator device 203 is provided in receptacle 123. Thus situated, the isolator devices are most effective in preventing contamination from leaving and entering their respective systems. That is, isolators 200 and 202 prevent bacterial and micro-organic contamination from escaping from the disposable flow system through the pressure communication channel. Isolator devices 201 and 203 prevent similar types of contamination from entering tubing segments 106 and 124 and transducers 107 and 125.

The integration factor provided in the pressure communication channels by the isolator elements is a function of the length and pore size of the elements. Increasing the length of the barrier and/or decreasing the pore size increases the amount of integration. Since the two isolator elements are effectively in series in their respective pressure communication channels, the combined effect of the two elements must be taken into account in determining the overall time constant provided to the system. In practice, it has been found that a time constant of from three to four seconds provides good immunity to transient pressure variations without unduely degrading the responsiveness of the TMP monitoring system to TMP pressure changes. This time constant can be obtained by providing a barrier having a length of 0.372 inch and a maximum diameter of 0.175 inch, and a pre size of 10 microns. Other time constants can be obtained by selecting different lengths and pre sizes of microporous barrier material.

Figure 9:
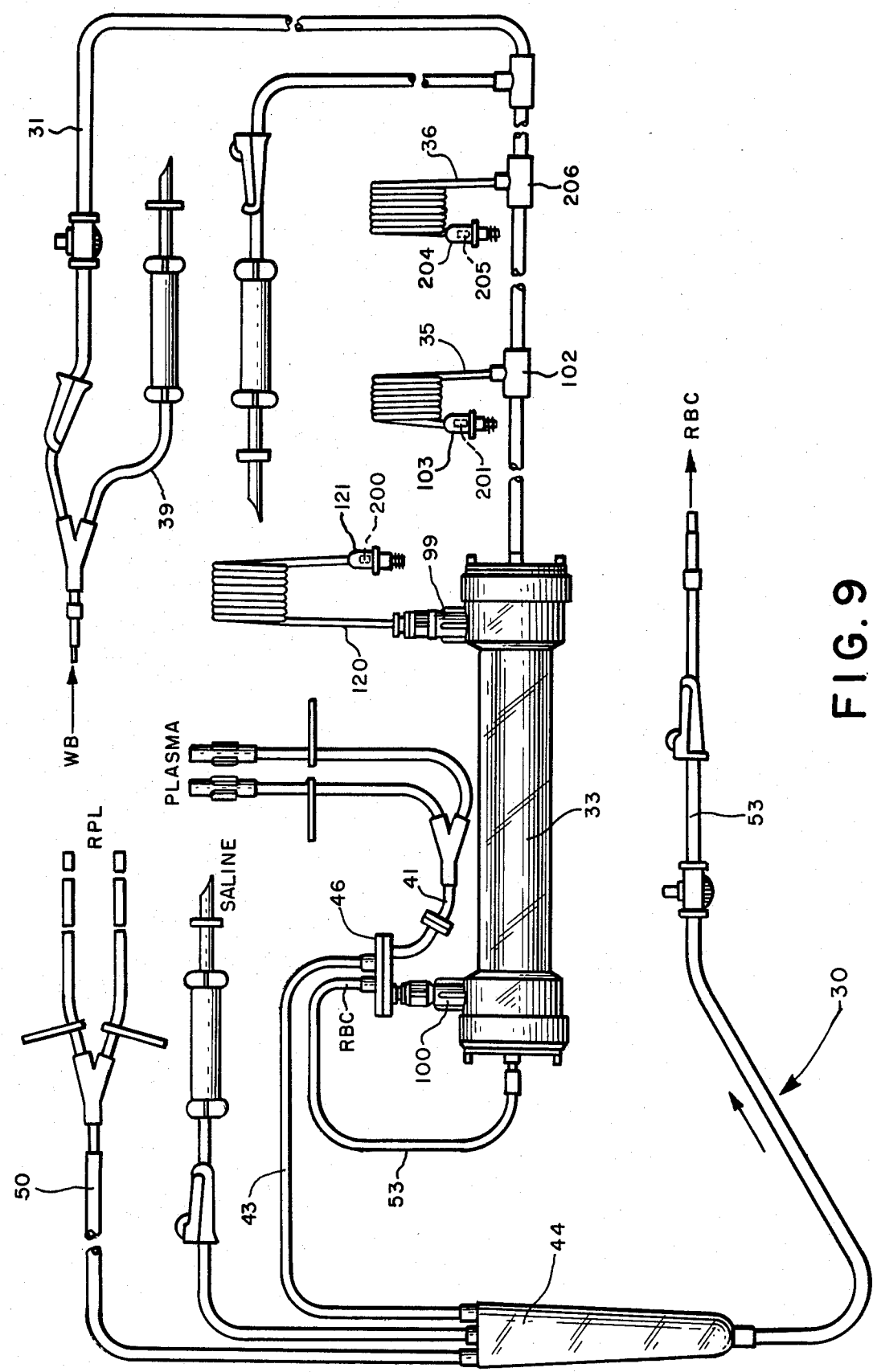
FIG. 9 is a pictorial representation of the disposable flow system utilized in conjunction with the plasmapheresis apparatus of FIG. 1 showing provisions made therein for the trans-membrane pressure monitoring system of the invention.

Providing isolator elements in plugs 103 and 121 may obviate the need for additional in-line filters in tubing segments 35 and 120. Since such in-line filters are comparatively more costly than the simple microporous barriers, a significant cost savings may be realized through use of the barriers in the disposable flow system. In FIG. 9 isolators 103 and 121 are shown as an integral part of the disposable flow system 30. Plug 103, which includes isolator element 201, is connected to a T-fitting by a section of tubing 35 of sufficient length such that during normal operation fluid in line 31 will not come into contact with isolator 201. During operation, the fluid advances through tubing 35 until an equilibrium point is reached, at which the back pressure exerted by the trapped air between the advancing fluid and the isolator is sufficient to prevent further advance of the fluid.

Similarly, connected 121 is connected to outlet port 99 of the hollow fiber membrane filter 33 with a tubing segment 120 of sufficient length to prevent the plasma collected within the filter device from coming into contact with isolator element 200 within the plug.

The negative pressure monitoring function may also advantageously employ an isolator element integral with the disposable flow set. As illustrated in FIG. 9, a plug 204 having an integral isolator element 205 may be provided at the end of tubing 36, which may be connected to tubing segment 31 by a conventional T-connector. As with the previously described monitoring functions, tubing segment 36 is preferably of sufficient length such that fluid in line 31 does not advance into contact with isolator element 205.

Figure 10:
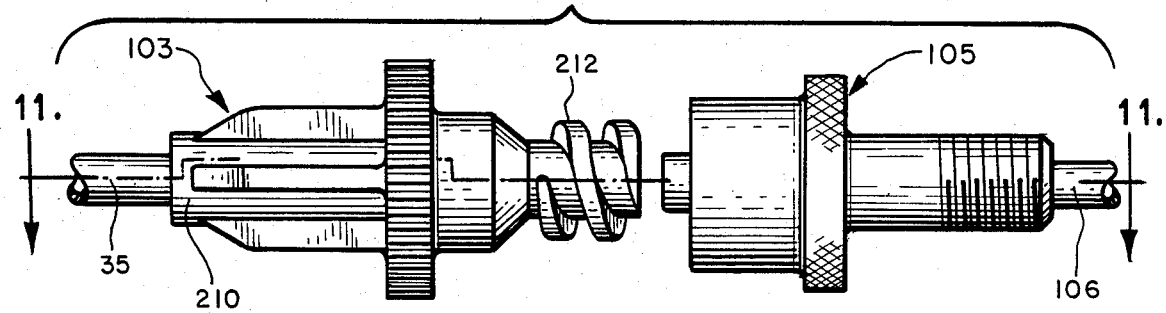
FIG. 10 is a front elevational view of a pressure transducer isolator utilized in the TMP monitoring system of the invention.
Figure 11:
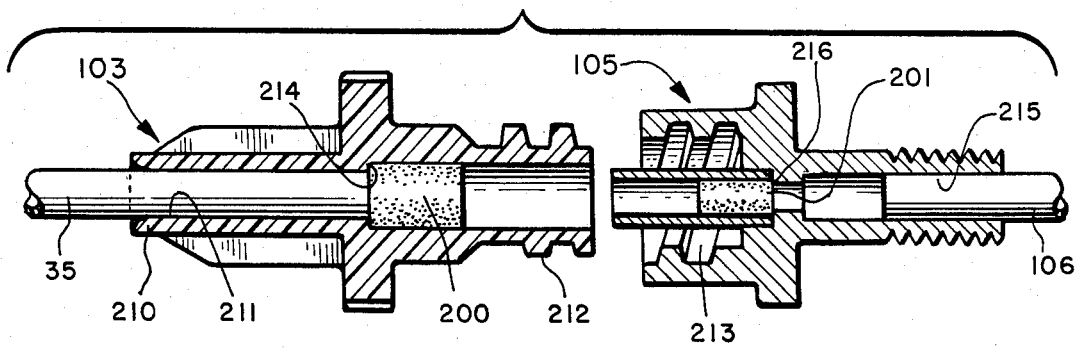
FIG. 11 is a cross-sectional view of the isolator taken along line 11—11 of FIG. 10.

As shown in FIGS. 10 and 11, isolator elements may be advantageously incorporated in their respective plug assemblies. More specifically, plug assembly 103, which may be identical to plug assemblies 121 and 204, includes a housing 210 having a central axially-aligned passageway 211 through which pressure communication is established. Tubing segment 35 connects to one end of the housing so as to establish communication with the central passageway. The other end of the housing includes a threaded projecting portion 212 which engages a complementarily threaded recess 213 on socket 105. A microporous isolator element generally cylindrical in form is positioned in passageway 211 against an internal rib portion 214 formed where the passageway increases in diameter.

Within socket 105 recess 213 communicates with a passageway 215 of reduced diameter. The microporous isolator element 201 is advantageously positioned against the rib 216 formed where the pressure communication passageway narrows. The tubing segment 106 provided to connect the socket to transducer 107 is bonded to the end of the socket by appropriate means.

Figure 12:
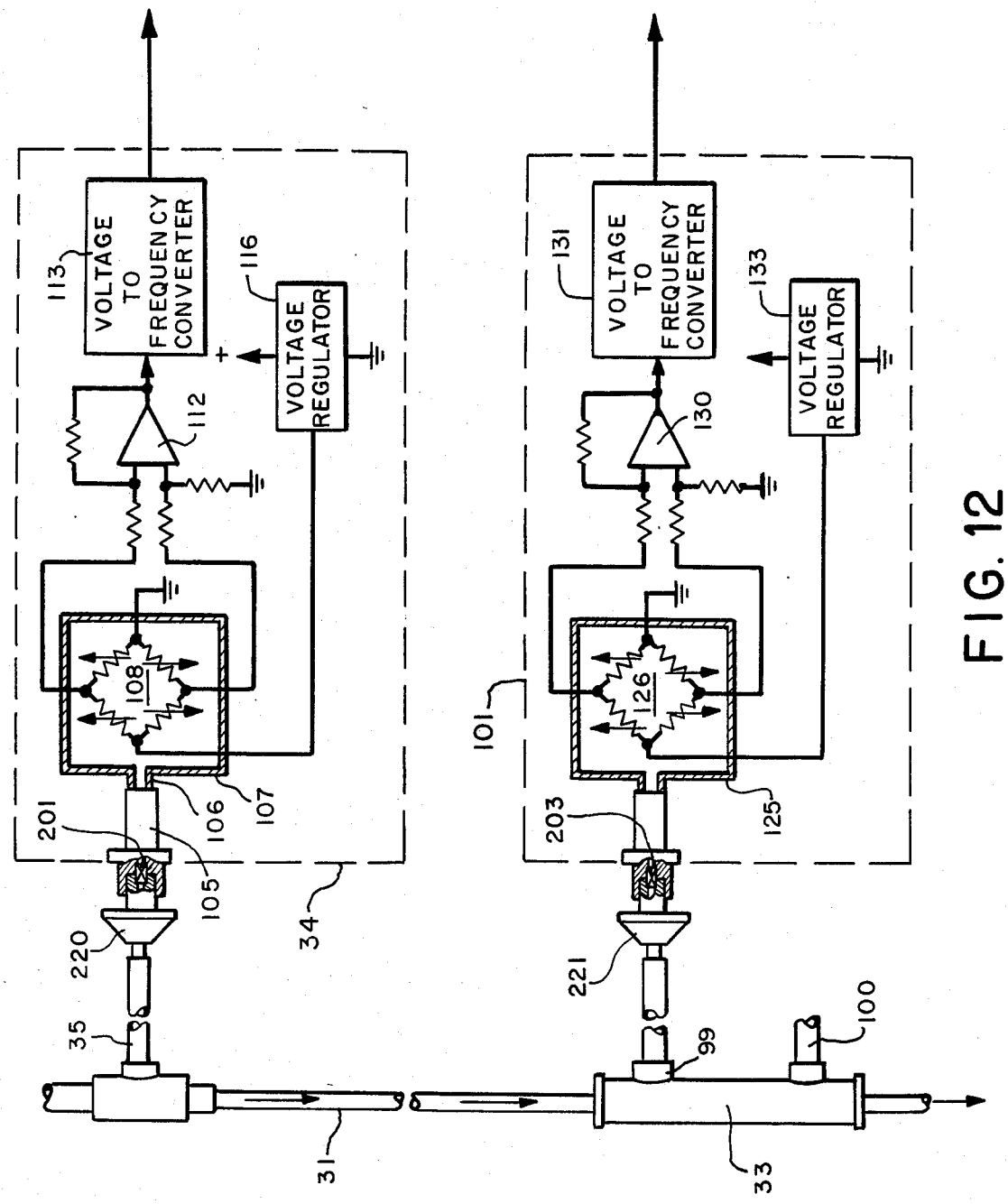
FIG. 12 is a simplified schematic diagram partially in functional block form showing an alternative construction for the TMP monitoring system of the invention.

While certain cost advantages exist for providing a microporous isolator element in the connectors associated with the three pressure monitoring functions provided for in the disposable flow system, it will be appreciated that other arrangements can be utilized for providing the necessary isolation and integration functions. For example, isolator elements could be provided at appropriate in-line location along tubing segments 35, 36 and 120 intermediate the ends thereof. Also, as illustrated in FIG. 12, the isolator elements could be eliminated from the pressure monitoring tubing segments 36 and 120 and in-line microporous hydrophobic filters 220 and 221 could be provided instead. With this arrangement it would be necessary to adjust the length and/or porosity of the remaining isolating elements 201 and 203 to provide the desired system time constants. The balance of the TMP monitoring system would remain identical in structure and operation to that previously described in connection with FIG. 6.

Figure 13:
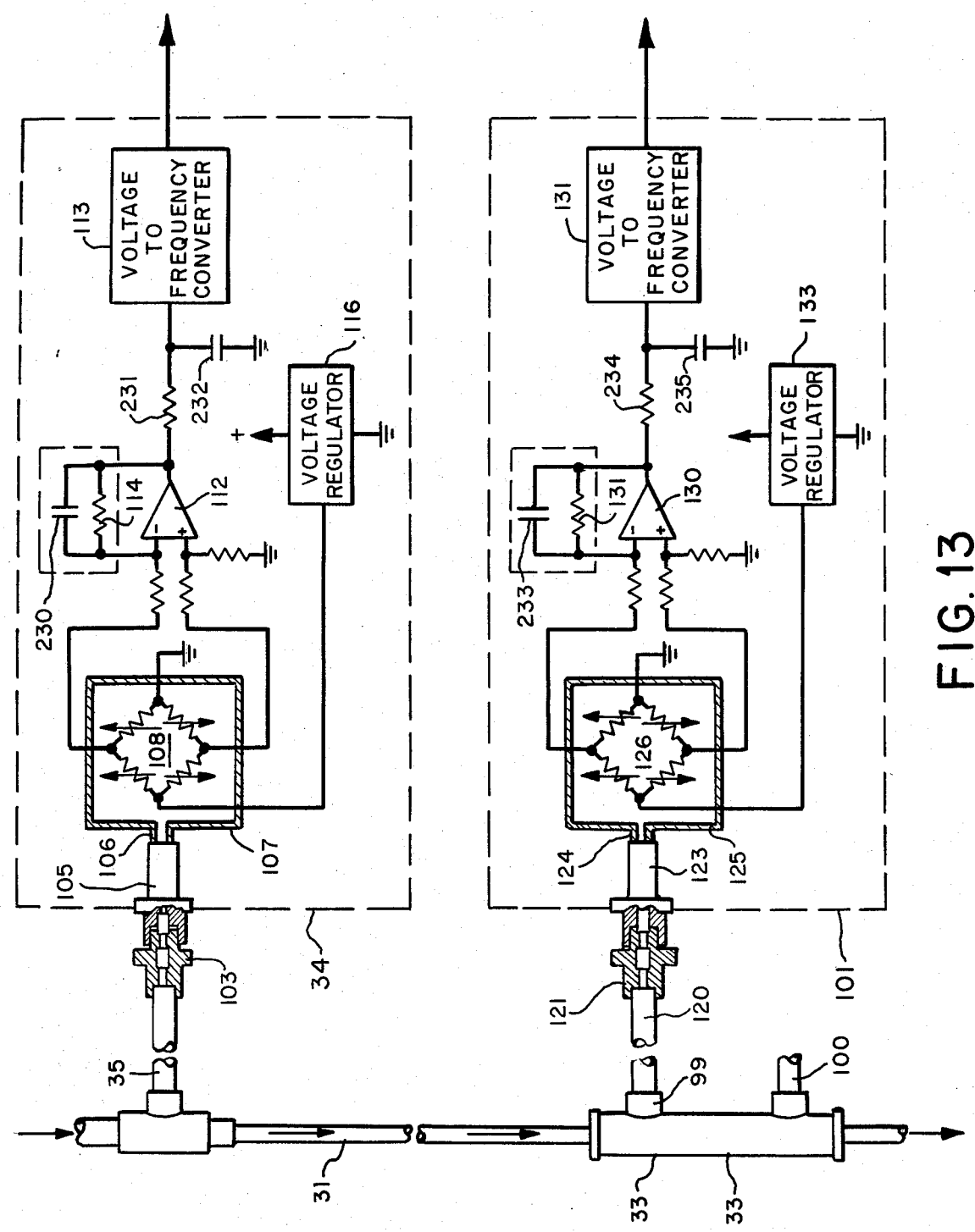
FIG. 13 is a schematic diagram similar to FIG. 12 showing a further alternative construction of the TMP monitoring system of the invention.

It is also possible to provide all or a portion of the integration provided by the isolator elements by means of electrical circuitry in the TMP monitoring system. Referring to FIG. 13, in the inlet pressure monitoring circuit, resistor 114 may be bridged by a capacitor 230 to provide a first RC time constant circuit. A resistor 231 may be connected between the output of diffential amplifier 112 and the input of voltage-to-frequency converter 113, and a capacitor 232 may be connected between the input of the converter 113 and ground, to provide a second RC time constant. Similarly, in the plasma pressure monitor circuit a capacitor 233 is connected in shunt cross resistor 131 to provide a first time constant circuit, and a resistor 234 and capacitor 235 are connected in the output circuit of differential amplifier 130 to provide a second time constant circuit.

The valves of resistors 114, 131, 231 and 234 and capacitors 230, 233, 232 and 235 are selected to provide an overall time constant for monitor circuits 34 and 101 of approximately three to four seconds.

It will be appreciated that it is also possible that circuity such as described in FIG. 13 would be required if the overall time constant introduced by one or more isolator elements in the respective pressure communication channels were not sufficient to in themselves provide the desired delay in the system. Such might be the case where isolator elements of physically small size are provided only in receptacles 105 and 123.

While particular embodiments of the invention have been shown and described, it will be obvious to those skilled in the art that changes and modifications may be made without departing from the invention in its broader aspects. For example, it would be possible to utilize the TMP monitoring system with flat plate microporous membrane type filters. The aim in the appended claims is to cover all such changes and modifications as fall within the true spirit and scope of the invention.

We claim:

1. A trans-membrane pressure monitoring system for use in conjunction with a fluid fractionation system of the type having a microporous membrane filter device including an inlet for whole fluid and an outlet for separated fluid component, comprising:

a first electrical transducer having an inlet port responsive to an applied pressure for producing a first pressure-indicative signal;

first pressure coupling means for establishing a pressure communication channel between said inlet port of said first electrical transducer and one side of said filter device;

a second electrical transducer having an inlet port responsive to an applied pressure for producing a second pressure-indicative signal;

second pressure coupling means for establishing a pressure communication channel between said inlet port of said second electrical transducer and the other side of said filter device;

each of said pressure coupling means including a first conduit portion integral with the associated side of said filter device, and a second conduit portion disconnectable from said first portion and integral with respective one of said transducers;

each of said coupling means further including in said first portion of a microporous barrier plug means for providing a determined integration constant in the associated one of said channels;

differential pressure derivation means responsive to said first and second pressure signals for producing an output signal indicative of the differential pressure across the membrane; and display means responsive to said output signal for displaying said differential pressure in operator readable format.

2. A pressure monitoring system as defined in claim 1 wherein said coupling means each include an additional microporous plug means in said second portion, said additional plug providing said predetermined time constant in conjunction with said barrier plug means in the associated first portion of each of said coupling means.

3. A trans-membrane pressure monitoring system for use in conjunction with a fluid fractionation system of the type having a microporous membrane filter device including an inlet for whole fluid and an outlet for separated fluid component, comprising:

a first electrical transducer having an inlet port responsive to an applied pressure for producing a first pressure-indicative signal;

first pressure coupling means for establishing a communication channel between said inlet port of said first electrical transducer and one side of said filter device, said coupling means including at least one microporous barrier plug providing a predetermined integration constant in said pressure communication channel;

a second electrical transducer having an inlet port responsive to an applied pressure for producing a second pressure-indicative signal;

second pressure coupling means for establishing pressure communication channel between said inlet port of said second electrical transducer and the other side of said filter device, said coupling means including at least one microporous barrier plug providing a predetermined integration constant in said pressure communication channel;

differential pressure derivation means responsive to said first and second pressure signals for producing an output signal indicative of the differential pressure across the membrane; and display means responsive to said output signal for displaying said differential pressure in operator readable format.

4. A pressure monitoring system as defined in claim 3 wherein said coupling means each include a first conduit portion integral with the flow system, and a second portion disconnectable from said first portion and integral with respective ones of said transducers, and said barrier plugs are included in said first portions.

5. A pressure monitoring system as defined in claim 4 wherein said first and second pressure means each include an additional barrier plug in said second portion, said additional plugs cooperating in providing said integration constant.

6. A pressure monitoring system as defined in claim 3 wherein said differential pressure derivation means are responsive to the difference of the pressures indicated by said pressure signals.

7. A trans-membrane pressure monitoring system for use in conjunction with a fluid fractionation system of the type having a microporous membrane filter device including an inlet for whole fluid and outlet for separated fluid component, comprising:

a first electrical transducer having an inlet port responsive to an applied pressure for producing a first pressure signal frequency-dependent on applied pressure;

first pressure coupling means for establishing a communication channel between said inlet port of said first electrical transducer and one side of said filter device;

a second electrical transducer having an inlet port responsive to an applied pressure for producing a second pressure signal frequency-dependent on applied pressure;

second pressure coupling means for establishing a pressure communication channel between said inlet port of said second electrical transducer and the other side of said filter device;

each of said pressure coupling means including a first conduit portion integral with the associated side of said filter device, and a second conduit portion disconnectable from said first portion and integral with respective one of said transducers;

each of said coupling means further including in said first portion of microporous barrier plug means for providing a predetermined integration constant in the associated one of said channels;

differential pressure derivation means responsive to the frequency between said first and second pressure signals for producing an output signal frequency dependent on the differential pressure across the membrane; and display means including a display counter responsive to said output signal for digitally displaying said differential pressure.

8. A pressure monitoring system as defined in claim 7 wherein said coupling means each include an additional microporous plug means in said second portion, said additional plug providing said predetermined time constant in conjunction with said barrier plug means in the associated first portion of each of said coupling means.

9. A pressure monitoring system as defined in claim 8 wherein the filter device is a hollow fiber device.

10. A trans-membrane pressure monitoring system for use in conjunction with a fluid fractionation system having a hollow-fiber microporous membrane filter device including an inlet for while fluid and an outlet for separated fluid component, comprising:

a first electrical transducer having an inlet port responsive to an applied pressure for producing a first pressure signal frequency-dependent on applied pressure;

first pressure coupling means for establishing a communication channel between said inlet port of said first electrical transducer and one side of said filter device, said coupling means including at least one microporous barrier plug providing a predetermined integration constant in said pressure communication channel;

a second electrical transducer having an inlet port responsive to an applied pressure for producing a second pressure signal frequency-dependent on applied pressure;

second pressure coupling means for establishing pressure communication channel between said inlet port of said second electrical transducer and the other side of said filter device, said coupling means including at least one microporous barrier plug providing a predetermined integration constant in said pressure communication channel;

differential pressure derivation means responsive to the frequency difference between said first and second pressure signals for producing an output signal frequency dependent on the differential pressure across the membrane; and display means including a display counter responsive to said output signal for digitally displaying said differential pressure.

11. A pressure monitoring system as defined in claim 10 wherein said coupling means each include a first conduit portion integral with the flow system, and a second portion disconnectable from said first portion and integral with respective ones of said transducers, and said barrier plugs are included in said first portions.

12. A pressure monitoring system as defined in claim 11 wherein said first and second pressure coupling means each include an additional barrier plug in said second portion, said additional plugs cooperating in providing said integration constant.

13. A pressure monitoring system as defined in claim 10 wherein the filter device is a hollow fiber device.

14. A trans-membrane pressure monitoring system for use in conjunction with a fluid fractionation system having a hollow-fiber microporous membrane filter device including an inlet for whole fluid, an outlet for whole fluid, and an outlet for separate fluid component, comprising:

a first electrical transducer having an inlet port responsive to an applied pressure for producing a first pressure signal frequency-dependent on applied pressure;

first pressure coupling means for establishing a communication channel between said inlet port of said first electrical transducer and the whole fluid inlet of said filter device, said coupling means including at least one microporous isolator providing a predetermined integration constant in said pressure communication channel;

a second electrical transducer having an inlet port responsive to an applied pressure for producing a second pressure signal frequency-dependent on applied pressure;

second pressure coupling means for establishing pressure communication channel between said inlet port of said second electrical transducer and the separated component outlet of said filter device, said coupling means including at least one microporous isolator providing a predetermined integration constant in said pressure communication channel;

pressure equalizer means coupled between the whole fluid inlet and the collected fluid outlet for monitoring a predetermined pressure differential between the whole fluid entering the filter and the plasma collected in the filter;

differential pressure derivation means responsive to said first and second pressure signals for producing an output signal indicative of the differential pressure across the membrane; and display means responsive to said output signal for displaying said differential pressure.

15. A pressure monitoring system as defined in claim 14 wherein said coupling means each include a first conduit portion integral with the flow system, and a second portion disconnectable from said first portion and integral with respective ones of said transducers, and said isolator elements are included in said first portions.

16. A pressure monitoring system as defined in claim wherein said first and second pressure coupling means such include an additional isolator element in said second portion, said additional plugs cooperating in providing said integration constant.

17. A trans-membrane pressure monitoring system as defined in claim 14 wherein said equalizer means is user-adjustable to maintain a selected pressure differential.

* * * * *